(12) United States Patent
Hotta et al.

(10) Patent No.: US 7,156,967 B2
(45) Date of Patent: Jan. 2, 2007

(54) GAS SENSOR ELEMENT CONTAINING A GETTER

(75) Inventors: Yasumichi Hotta, Mie-pref. (JP); Namitsugu Fujii, Yokkaichi (JP); Gang E, deceased, late of Suita (JP); by Xin Fu, legal representative, Suita (JP)

(73) Assignee: Denso Corporation, Kariya (JP)

( * ) Notice: Subject to any disclaimer, the term of this patent is extended or adjusted under 35 U.S.C. 154(b) by 364 days.

(21) Appl. No.: 10/308,173

(22) Filed: Dec. 3, 2002

(65) Prior Publication Data
US 2004/0007462 A1    Jan. 15, 2004

(30) Foreign Application Priority Data
Dec. 3, 2001  (JP) .............................. 2001-368815
Oct. 3, 2002  (JP) .............................. 2002-291519

(51) Int. Cl.
*G01N 27/407*    (2006.01)
(52) U.S. Cl. ..................... 204/429; 73/23.32
(58) Field of Classification Search ................ 204/424, 204/428, 429; 73/23.31, 23.32
See application file for complete search history.

(56) References Cited
U.S. PATENT DOCUMENTS
4,021,326 A * 5/1977 Pollner et al. .............. 204/429

4,584,086 A * 4/1986 Hayakawa et al. ......... 204/429
5,368,713 A    11/1994 Friese et al.
5,593,558 A * 1/1997 Sugino et al. .............. 204/429
5,849,165 A * 12/1998 Kojima et al. .............. 204/429
6,409,899 B1 * 6/2002 Satou et al. ................ 204/429

FOREIGN PATENT DOCUMENTS
JP    6-502014    3/1994
JP    8-10210     1/1996

OTHER PUBLICATIONS
Roberts et al, Encyclopedia of Minerals, 2nd Edition, 1990, pp. 199, 709-711, 881 and 882.*

* cited by examiner

*Primary Examiner*—Kaj K. Olsen
(74) *Attorney, Agent, or Firm*—Nixon & Vanderhye P.C.

(57) ABSTRACT

The present invention provides a gas sensor element and its production method, in which poisons are trapped in a porous protective layer to prevent them from reaching a measured gas side electrode, thereby making it possible to maintain a stable sensor output over a long period of time.

The gas sensor element of the present invention is composed of a solid electrolyte 10, and a measured gas side electrode 12 that contacts a measured gas and a reference gas side electrode 11 that contacts a reference gas provided on said solid electrolyte 10; wherein, the above measured gas side electrode 12 is covered with a porous protective layer 14 composed of a heat-resistant metal oxide containing a getter, and the above getter is an alkaline silicate.

12 Claims, 5 Drawing Sheets

GAS SENSOR ELEMENT CONTAINING A GETTER

BACKGROUND OF THE INVENTION

1. Field of the Invention

The present invention relates to a gas sensor element and its production method that is built inside an oxygen sensor and so forth which detects the oxygen concentration in exhaust gas that is intimately related to the air-fuel ratio of an air-fuel mixture supplied for combustion in, for example, an internal combustion engine.

2. Description of the Related Art

Gas sensor elements of the oxygen variable concentration electromotive force type that use a $ZrO_2$ solid electrolyte are well known practical examples of gas sensor elements containing a built-in oxygen sensor that are used by installing in the exhaust pipe of an automobile engine.

A gas sensor element capable of detecting oxygen is provided in the leading end of the above oxygen sensor, and the gas sensor element is composed of a bottomed, cylindrical solid electrolyte, a reference gas side electrode on the inside of a reference gas chamber provided inside said solid electrolyte, a measured gas side electrode on the outside of the above solid electrolyte, and a porous protective layer that covers said measured gas side electrode.

A heater may be inserted in the reference gas chamber provided inside the above gas sensor element. The above porous protective layer is composed of multiple layers provided with, for example, a ceramic coating layer or ceramic coating layer and, for example, a $\gamma$-$Al_2O_3$ layer thereon.

Exhaust gas that passes through an exhaust pipe passes over the above ceramic coating layer and the above $\gamma$-$Al_2O_3$ layer and reaches the above measured gas side electrode to obtain a sensor output.

However, due to the increasingly severe regulations on emissions in recent years, it has become necessary to control engine combustion more precisely. Consequently, it has become an indispensable condition for gas sensor elements used by containing within an oxygen sensor of the exhaust pipe of an automobile engine to be more stable without changing sensor characteristics despite being exposed to a more severe working environment.

After exhaust gas containing unburnt components has reached the measured gas side electrode, an equilibrium oxygen concentration is obtained due to the occurrence of an oxidation reaction on this electrode, and the output of the gas sensor element is generated according to the difference between this concentration and the oxygen concentration of the atmosphere that has entered the reference gas chamber.

An important characteristic of a gas sensor element output is the $\lambda$ point at which the output shown in FIG. 4 changes rapidly. Although automobile engine control using an oxygen sensor consists of feedback control by making a judgment of rich or lean with respect to a reference voltage, in order to perform said feedback control precisely, it is extremely important that the above point at which $\lambda$ changes suddenly (to be referred to as "control $\lambda$") be stabilized. In other words, it is important that control $\lambda$ always be at a specific position on the curve shown in FIG. 4 regardless of changes in the external atmosphere. Moreover, the responsiveness of the gas sensor element to lean and rich changes is similarly important.

The main factor that causes changes in sensor characteristics such as control $\lambda$ and responsiveness as mentioned above in the actual usage environment is impaired electrode activity due to the surface of the measured gas side electrode being covered by poisons such as Pb, S and other components of the gasoline used as fuel, as well as gaseous phase silicon (Si) and so forth generated from Si components contained in gaskets and oil and engine seals, that have passed through the porous protective layer of the gas sensor element and reached the surface of the measured gas side electrode.

Furthermore, this phenomenon is also referred to as poisoning deterioration of a gas sensor element.

Japanese Examined Patent Publication No. 8-10210 proposes a method for preventing deterioration of sensor characteristics caused by Si poisoning by containing an Si reactive component comprised of one or more types of IIIa subgroup elements of the periodic table and their compounds (excluding oxides) in a porous protective layer base material.

The above art offers the effect of preventing adherence of Si only by chemically reacting Si components.

However, in cases of more severe endurance conditions, in other words, when exposed for long periods of time to Si or other poisons at high concentrations, the prior art is unable to obtain adequate effects for preventing Si poisoning, thus resulting in the problem of conspicuous deterioration of the gas sensor element.

Since compounds containing IIIa subgroup elements and silicates of IIIa subgroup elements typically have a comparatively high melting point, they cannot be said to be adequately effective in trapping Si and other poisons in a porous protective layer under conditions of low temperature, high Si concentration and a long endurance period.

Japanese Unexamined International Patent Publication No. 6-502014 is another example of the prior art.

This publication describes the generation of an advantageous gettering action in opposition to Si, Pb and other poisons by containing a mixed oxide comprised of an alkaline metal oxide and heat-stable metal oxide containing a trivalent element in a porous protective layer of a gas sensor element.

However, in this example of the prior art, since the gettering material (material that primarily traps poisons) is a mixed oxide of an alkaline metal oxide and trivalent or tetravalent oxide, when used for a long period of time, free alkaline oxide components become unstable due to a usage environment in which the gas sensor element is exposed to rapid temperature changes and atmospheric changes, resulting in increased susceptibility to changes in other stable compounds such as alkaline carbonates and hydroxides.

In the case a free alkaline oxide component has changed, the volume expands which leads to clogging of the porous protective layer and separation of the porous protective layer, thereby resulting in the risk of a decrease in the poison trapping action and a decrease in the responsiveness of the gas sensor element.

In this manner, in the case of the poison trapping technology of the prior art, it was difficult to maintain a stable gas sensor element output over a long period of time under conditions such as a low atmospheric temperature or high poison concentration and so forth.

SUMMARY OF THE INVENTION

In consideration of the above problems of the prior art, the object of the present invention is to provide a gas sensor element, and its production method, in which poisons are trapped in a porous protective layer to prevent them from reaching a measured gas side electrode, thereby making it possible to maintain a stable sensor output over a long period of time.

A first aspect of the invention is a gas sensor element comprising: a solid electrolyte, and a measured gas side electrode that contacts measured gas and a reference gas side electrode that contacts a reference gas provided on said solid electrolyte; wherein,
 the above measured gas side electrode is covered with a porous protective layer composed of a heat-resistant metal oxide containing a getter, and
 the above getter is an alkaline silicate.

A second aspect of the invention is a gas sensor element composed of a solid electrolyte, and a measured gas side electrode that contacts a measured gas and a reference gas side electrode that contacts a reference gas provided on said solid electrolyte; wherein,
 the above measured gas side electrode is covered with a porous protective layer composed of a heat-resistant metal oxide containing a getter, and
 the above getter is crystalline silica.

A third aspect of the invention is a gas sensor element composed of a solid electrolyte, and a measured gas side electrode that contacts a measured gas and a reference gas side electrode that contacts a reference gas provided on said solid electrolyte; wherein,
 the above measured gas side electrode is covered with a porous protective layer composed of a heat-resistant metal oxide containing a getter, and
 the above getter is composed of the two types of alkaline silicate and crystalline silica.

A fourth aspect of the invention is a gas sensor element composed of a solid electrolyte, and a measured gas side electrode that contacts a measured gas and a reference gas side electrode that contacts a reference gas provided on said solid electrolyte; wherein,
 the above measured gas side electrode is covered with a porous protective layer composed of a heat-resistant metal oxide containing a getter, and
 the above getter is composed of one or more types of compounds containing a metal and/or compound capable of trapping Si and/or an Si-containing compound, and a metal and/or compound capable of trapping Pb and/or a Pb-containing compound.

A fifth aspect of the invention is a gas sensor element composed of a solid electrolyte, and a measured gas side electrode that contacts a measured gas and a reference gas side electrode that contacts a reference gas provided on said solid electrolyte; wherein,
 the above measured gas side electrode is covered with a porous protective layer composed of a heat-resistant metal oxide containing a getter,
 the above getter is a compound oxide, and,
 said compound oxide is composed of an alkaline metal oxide and a pentavalent or hexavalent transition metal oxide.

In the first through fifth aspects of the invention, a measured gas side electrode is covered with a porous protective layer composed of a heat-resistant metal oxide, and this porous protective layer composed of a heat-resistant metal oxide contains a getter.

As a result of conducting earnest studies particularly on the trapping of gaseous phase poisons (and primarily Si and Pb), the inventors of the present invention determined that, by using each of the above compounds that are comparatively more stable than alkaline oxides as a getter, the getter is able to trap gaseous phase poisons such as Si and Pb particularly at low temperatures by reacting with them, thereby being particularly effective in preventing poisoning of the measured gas side electrode.

Moreover, a porous protective layer containing the above getter is resistant to clogging of the porous protective layer as well as impaired gas permeability when a poison has been trapped in the porous protective layer. Accordingly, the gas sensor element is resistant to decreases in responsiveness even when exposed to measured gases for long periods of time.

As has been described above, according to the present invention, a gas sensor element can be provided in which poisons are trapped in a porous protective layer containing a getter to prevent the poisons from reaching the measured gas side electrode, thereby making it possible to maintain a stable sensor output over a long period of time.

A sixth aspect of the invention is a production method of a gas sensor element comprising: during production of a gas sensor element composed of a solid electrolyte, and a measured gas side electrode that contacts a measured gas and a reference gas side electrode that contacts a reference gas provided on the solid electrolyte, in the covering of the above measured gas side electrode with a porous protective layer composed of a heat-resistant metal oxide containing a getter,
 at least one layer is formed of a porous protective layer composed of a heat-resistant metal oxide by covering the above measured gas side electrode with a heat-resistant metal oxide,
 followed by impregnating a solution containing a getter raw material component to serve as the getter into the above porous protective layer composed of a heat-resistant metal oxide by heat treatment and then subsequently performing drying and heat treatment to obtain a porous protective layer composed of a heat-resistant metal oxide containing the above getter.

A seventh aspect of the invention is a production method of a gas sensor element comprising: during production of a gas sensor element composed of a solid electrolyte, and a measured gas side electrode that contacts a measured gas and a reference gas side electrode that contacts a reference gas provided on the solid electrolyte, in the covering of the above measured gas side electrode with a porous protective layer composed of a heat-resistant metal oxide containing a getter,
 a porous protective layer material composed of a heat-resistant metal oxide containing a getter raw material component is plasma coated to obtain a porous protective layer composed of a heat-resistant metal oxide containing a getter.

An eighth aspect of the invention is a production method of a gas sensor element comprising: during production of a gas sensor element composed of a solid electrolyte, and a measured gas side electrode that contacts a measured gas and a reference gas side electrode that contacts a reference gas provided on the solid electrolyte, in the covering of the above measured gas side electrode with a porous protective layer composed of a heat-resistant metal oxide containing a getter,
 a porous protective layer material composed of a heat-resistant metal oxide containing a getter raw material component is formed into a slurry, and the resulting slurry is coated followed by drying and heat treatment to obtain a porous protective layer composed of a heat-resistant metal oxide containing a getter.

According to the sixth to eighth aspects of the invention, poisons are trapped in a porous protective layer containing a getter to prevent the poisons from reaching the measured gas side electrode, thereby making it possible to provide a production method of a gas sensor element capable of maintaining stable sensor output over a long period of time.

DESCRIPTION OF THE PREFERRED EMBODIMENTS

Figure 1:
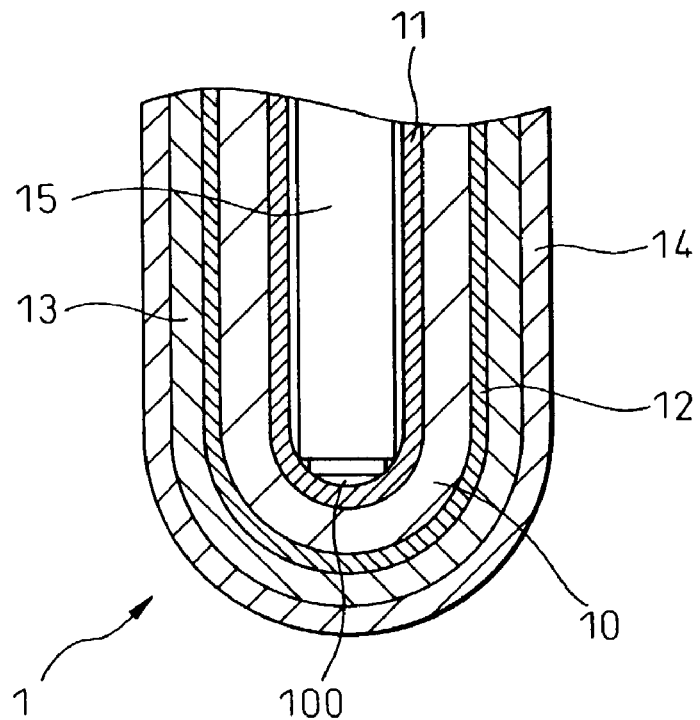
FIG. 1 is an explanatory drawing of a gas sensor element in Embodiment 1.

The first aspect of the invention uses alkaline silicate for the getter, while the second aspect of the invention uses crystalline silica. In addition, the third aspect of the invention uses both alkaline silicate and crystalline silica for the getter.

In the porous protective layer as claimed in the first aspect of the invention, due to the strong alkalinity of the alkaline silicate, more stable crystals of alkaline silicate are formed having a high Si content by reacting with silica (namely, $SiO_2$) even at comparatively low temperatures. At high temperatures, these crystals act as crystal nuclei that stabilize amorphous $SiO_2$ formed by excess Si components and adsorb it onto the surface of crystal nuclei to crystallize the amorphous $SiO_2$, thereby trapping the silica.

In addition, in the porous protective layer as claimed in the second aspect of the invention, in the case the getter is crystalline silica, since the crystalline silica mainly functions as crystal nuclei, Si components can be easily adsorbed onto the surface of the crystalline silica. In this manner, by using crystalline silica as a getter instead of in a chemical reaction, amorphous $SiO_2$ is trapped as a result of being crystallized.

In the third aspect of the invention that has a porous protective layer containing both alkaline silicate and crystalline silica, poisons can be efficiently trapped in the porous protective layer by utilizing both of the above actions and effects.

In addition, the getter as claimed in the fourth aspect of the invention is composed of one or more types of either (a) or (b). In addition, the getter may also be composed of a complex compound composed of both compounds (a) and (b), and if it is a material that provides the function of a trap of Si and/or Si compounds and a trap of Pb and/or Pb-containing compounds with a one type of compound, a getter can be composed from a compound that contains it.

Here, (a) is a metal and/or compound capable of trapping Si and/or Si-containing compounds, while (b) is a one or more types of compounds containing a metal and/or compound capable of trapping Pb and/or Pb-containing compounds.

Examples of compounds pertaining to (a) that can be used include alkaline silicates, crystalline silica and so forth to be described later, while examples of compounds pertaining to (b) that can be used include pentavalent or hexavalent transition metal oxides such as $WO_3$, $MoO_3$ and $Nb_2O_5$.

In addition, the getter of the porous protective layer as claimed in the fifth aspect of the invention is a complex compound. This complex compound is composed of an alkaline metal oxide and a pentavalent or hexavalent transition metal oxide.

Alkaline metal oxides react well with poison components such as Si or Pb at low temperatures, and since their boiling point is relatively lower than silicates, they react with components in poisons at low temperatures and are capable of adequately trapping them.

Pentavalent or hexavalent transition metal oxides are capable of adequately trapping divalent elements such as Pb contained in poisons.

Since the getter as claimed in the fifth aspect of the invention is present in the form of a comparatively stable compound in a state in which these poisons have been trapped, the effect of trapping poisons does not diminish even in long-term endurance or even if exposed to severe temperature changes and atmospheric conditions.

In addition, since the products of reaction with poisons are fine crystals and not amorphous, clogging of the porous protective layer due to adherence of amorphous products is prevented.

Next, an explanation is provided regarding the porous protective layer composed of a heat-resistant metal oxide as claimed in the first through fifth aspects of the invention.

The above porous protective layer is preferably composed of a mixture of coarse particles and fine particles of a heat-resistant metal oxide. As a result of fine particles entering into the gaps between the coarse particles, the porosity and pore diameter of the porous protective layer can be made to be adequately small.

In addition, since corresponding coarse particles are able to prevent the occurrence of cracking by forming bridges between them during formation of the porous protective layer, a porous protective layer of adequate thickness can be easily obtained.

At this time, the ratio of the average particle diameter (RB) of the coarse particles to the average particle diameter (RA) of the fine particles (RB/RA) is preferably 5 or more.

The above fine particles are preferably solid solution particles containing one or more types selected from $\gamma$-$Al_2O_3$, $\theta$-$Al_2O_3$ and $\delta$-$Al_2O_3$ having a specific surface area of 50 m2/g or more.

In addition, with respect to the composite ratio of coarse particles and fine particles, if the weight ratio (value of WA/W) of the fine particle content (WA) to the total weight W of the above coarse particle contents (WB) and the fine particle content (WA) (=WA+WB) is 20 or more, a rigid porous protective layer can be obtained, thereby making this preferable.

In addition, since the porous protective layer as claimed in the first, third and fifth aspects of the invention contains a 1$a$ subgroup element (alkaline metal) and its compounds, it can be provided with high poisoning preventive effects along with superior heat resistance.

The first through fifth aspects of the invention can be applied to a cup type gas sensor element provided with a reference gas side electrode and measured gas side electrode on a bottomed, cylindrical solid electrolyte as will be described later. Alternatively, they can also be applied to a plate-shaped gas sensor element composed by providing a reference gas side electrode and measured gas side electrode on a plate-shaped solid electrolyte.

Furthermore, although the embodiments and so forth are described with respect to a gas sensor element that measures oxygen concentration, the present invention can also be applied generally to gas sensor elements used in atmospheres in which poisons are present in a measured gas.

In addition, the present invention can also be applied regardless of the type of gas sensor element, such as to a compound gas sensor element capable of detecting a plurality of types of gas concentrations, an NOx sensor element, an HC sensor element or a CO sensor element.

In addition, although the gas sensor elements described in the embodiments are sensors of the variable oxygen concentration electromotive type, the present invention can also be applied to sensors of the critical current type. Furthermore, examples of sensors of the critical current type include those used as so-called air-fuel ratio sensor elements and those used as lean sensors.

In addition, in the first and third aspects of the invention, the above alkaline silicate is preferably one or more types selected from lithium orthosilicate ($Li_4SiO_4$), lithium metasilicate ($Li_2SiO_3$), lithium disilicate ($Li_2Si_2O_3$), hexalithium disilicate ($Li_6Si_2O_7$), $Li_2Si_3O_7$ and $Li_8SiO_6$.

The above-mentioned lithium silicates are fine compound crystalline particles. Since said lithium silicates have comparatively strong alkalinity, they react with $SiO2$ even at comparative low temperatures, and sequentially change to more stable alkaline silicate crystals having a high Si content such as $Li_2SiO_3$ and $Li_2Si_2O_5$.

Moreover, since these $Li_2SiO_3$, $Li_2Si_2O_5$ and so forth have a comparatively high melting point of their reaction products, and a cyclic structure in which Si—O bonds expand two-dimensionally or three-dimensionally, they function as crystal nuclei, and together with advantageously trapping the next Si component by adsorbing and reacting with it, stably crystallize amorphous $SiO_2$ resulting from excess Si components at high temperatures.

Consequently, the are able to efficiently trap poisons, and have superior endurance since there is no occurrence of clogging of the porous protective layer caused by trapping. Accordingly, a gas sensor element can be obtained that is capable of maintaining a stable sensor output over a long period of time.

In addition, in the second and third aspects of the invention, the above crystalline silica is preferably one or more types selected from silica fine crystals, tridymite, cristobalite and quartz.

Similar to the above-mentioned alkaline silicate, in the case of using these materials as crystalline silica, these materials function primarily as crystal nuclei, and easily trap Si components on their surfaces. This trapping is the result of crystallizing amorphous $SiO_2$ on the surface of crystal nuclei composed of these materials without being accompanied by a chemical reaction. In addition, due to the fine particle diameter of these materials, they have a wide surface area that enables trapping to be carried out efficiently.

In addition, since the products of reacting with poisons are fine crystals instead of being amorphous, clogging of the porous protective layer caused by adherence of amorphous products is prevented.

Accordingly, poisons are trapped in the porous protective layer and are prevented from reaching the measured gas side electrode, thereby making it possible to maintain a stable sensor output over a long period of time.

In addition, in the fifth aspect of the invention, the above complex compound is preferably a tungstenate salt of an alkaline metal or a molybdenate compound of an alkaline metal.

More particularly, the above complex compound is preferably one or more types selected from $Li_2W_4O_{13}$, $Li_2W_2O_7$, $Li_2WO_4$, $Li_4WO_5$, $Li_6W_2O_9$, $Li_2WO_6$, $Li_6WO_6$, $Li_2MoO_4$, $Li_2Mo_4O_{13}$, $Li_4MoO_5$ and $Li_2Mo_2O_7$.

$Li_2MoO_4$, $Li_2Mo_4O_{13}$ and so forth are molybdenate salts, while $Li_2WO_4$, $Li_2W_4O_{13}$, $Li_2W_2O_7$, $Li_4WO_5$ and so forth are tungstenate salts.

Since these salts have high reactivity with poisons such as Si and Pb, and their melting points are relatively lower than silicates, alkaline components are able to react easily with Si components at low temperatures.

Moreover, tungsten and molybdenum are able to trap divalent elements, and are able to trap poisons such as Pb.

In addition, together with these substances having high reactivity with Si and other poisons starting at low temperatures, since they are present in the form of comparatively stable compound forms, the effect of trapping poisons is not diminished easily even with respect to long-term endurance and exposure to severe temperature changes and atmospheric conditions.

In addition, since the reaction products formed with the poisons are fine crystals and not amorphous, they are also effective in preventing clogging of the porous protective layer caused by adherence of amorphous products, thereby enabling a gas sensor element to obtain a stable output over a long period of time.

In addition, in the first through fifth aspects of the invention, the content of the above getter with respect to the above porous protective layer composed of a heat-resistant metal oxide is preferably 0.3–70 wt %.

As a result, a porous protective layer can be obtained that is capable of adequately trapping poisons.

If the content of the above getter is less than 0.3 wt %, there is the risk of the above porous protective layer being unable to adequately trap poisons, while if the content exceeds 70 wt %, the thermal stability of the porous protective layer is impaired, and there is the risk of decreased heat resistance.

Furthermore, the above content is defined in the following manner. Namely, if the weight of the entire porous protective layer that contains a getter is taken to be WT, and the weight of the getter is taken to be WG, then the above content is $\{(WG/WT) \times 100\}$ (wt %).

In addition, in the first through fifth aspects of the invention, the thickness of the above porous protective layer composed of a heat-resistant metal oxide is preferably 20–300 µm.

As a result, a gas sensor element can be obtained that has superior responsiveness and is capable of adequately trapping poisons.

In the case the thickness of the porous protective layer is 20 µm or less, the length of the path over which the measured gas passes becomes shorter, thereby resulting in the risk of toxins being unable to be adequately trapped, while in the case the thickness exceeds 300 µm, the length of the path over which the measured gas passes becomes excessively long, thereby resulting in the risk of decreased responsiveness of the gas sensor element.

In addition, in the first through fifth aspects of the invention, the average particle diameter of the above getter is preferably 0.1–1 µm.

As a result, a getter can be obtained that is stable and resistant to the occurrence of aggregation caused by heating. In the case the average particle diameter of the getter is less than 0.1 µm, there is the risk of the getter being aggregated by heat which may cause it to lose its trapping effect. In addition, in the case the average particle diameter exceeds 1 µm, there is the risk of the specific surface area decreasing, which is turn can cause a decrease in poison trapping efficiency.

In addition, in the first through fifth aspects of the invention, the above porous protective layer composed of a heat-resistant metal oxide preferably contains a matrix composed of one or more types of a particulate material selected from $\gamma$-$Al_2O_3$, $\theta$-$Al_2O_3$ and $\delta$-$Al_2O_3$.

Since alumina having these crystal forms has an extremely high ability to adsorb Si and other gaseous phase poisons because of its large specific surface area of 50 $m^2/g$ or more, the reaction between a getter contained in the porous protective layer and a poison can be made to take place efficiently.

Moreover, since there is no occurrence of clogging of the porous protective layer, poisons can be converted to stable silicate and other crystals, and the porous protective layer has a uniform compound structure, the porous protective layer is given superior thermal stability and endurance.

Moreover, in the case of containing each of the above getters in a porous protective layer composed of alumina, and particularly in the case the getter is an alkaline silicate or compound oxide, in addition to Li (Na, K)—Si—O-based compounds, Li (Na,K)—Si—Al—O-based compounds are generated in the poison trapping process.

Since these Li (Na,K)—Si—Al—O-based compounds have a comparatively high melting point in the crystalline state, there is no occurrence of decomposition, melting and so forth at temperatures of about 1000° C. that exceed the maximum working temperature of ordinary gas sensors.

Thus, as a result of a poison being trapped in the porous protective layer, together with there being no occurrence of clogging in the porous protective layer, the heat resistance of the porous protective layer can be enhanced.

Furthermore, the above porous protective layer may be composed only of a different crystal form of alumina in the manner of the $\gamma$, $\theta$ or $\delta$ form, or composed of a mixture of these crystal forms.

The first through fifth aspects of the invention preferably have at least one of the above porous protective layer composed of a heat-resistant metal oxide that contains a getter in direct contact with a measured gas side electrode. Alternatively, it preferably has another porous protective layer composed of a heat-resistant metal oxide that does not contain a getter between the above measured gas side electrode and the above porous protective layer composed of a heat-resistant metal oxide.

Figure 7:
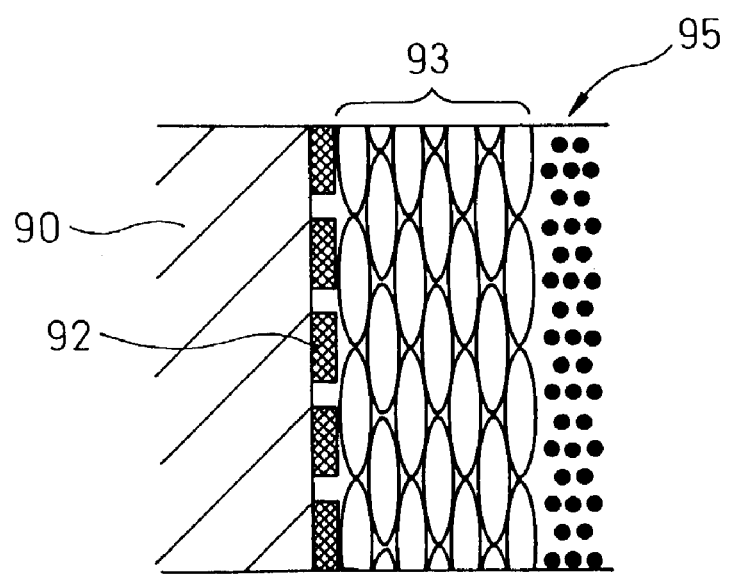
FIG. 7 is an explanatory drawing of the essential portion of a gas sensor element provided with a layer of a mixed oxide on a porous protective layer in an example of the prior art.

Namely, the first through fifth aspects of the invention can be applied to an element provided with a constitution in which a porous protective layer not containing a getter is laminated onto a measured gas side electrode, followed by laminating a porous protective layer containing a getter thereon (refer to FIG. 7 to be described later). In addition, it can also be applied to an element provided with a constitution in which a porous protective layer containing a getter is laminated directly onto a measured gas side electrode (refer to FIG. 2 to be described later). In addition, it can be applied to an element provided with a constitution in which a porous protective layer containing a getter is laminated directly onto a measured gas side electrode, and a porous protective layer not containing a getter thereon.

In addition, in the production method as claimed in the sixth aspect of the invention, a porous protective layer not containing a getter is provided on a measured gas side electrode, and processing is subsequently carried out that causes a getter to be contained in that porous protective layer. At this time, two or more layers of a porous protective layer may be provided on a measured gas side electrode, and a getter may only be contained in the porous protective layer of the uppermost layer. In addition, a different porous protective layer may also be provided after providing a porous protective layer and containing a getter therein.

In addition, the seventh and eighth aspects of the invention are methods for forming a porous protective layer containing a getter in a single step, with a porous protective layer being produced using plasma coating in the seventh aspect of the invention, and using slurry coating in the eighth aspect of the invention. Furthermore, slurry coating can be carried out by dipping or spraying.

In the case of composing a porous protective layer containing a getter in a single step, the getter can be more strongly fixed in the gas sensor element by the porous protective layer material acting as an aggregate.

In the seventh and eighth aspects of the invention, it is preferable to provide a porous protective layer composed of a heat-resistant metal oxide not containing a getter that directly covers the above measured gas side electrode, followed by providing a porous protective layer composed of a heat-resistant metal oxide that contains a getter so as to directly cover said porous protective layer.

Namely, although a porous protective layer containing a getter can also be formed directly on a measured gas side electrode, a porous protective layer containing a getter can also be provided on that which is provided with a porous protective layer not containing a getter.

In addition, in the sixth through eighth aspects of the invention, the above getter is preferably composed of one or more types selected from alkaline silicate, crystalline silica and compound oxide composed of alkaline metal oxide and pentavalent or hexavalent transition metal oxide.

As a result, effects can be obtained corresponding to the type of the above getter, and poisons can be trapped in the porous protective layer and prevented from reaching the measured gas side electrode, thereby allowing the production of a gas sensor element capable of maintaining stable sensor output over a long period of time.

The following provides an explanation of the embodiments of the present invention using the drawings.

Embodiment 1

Figure 2:
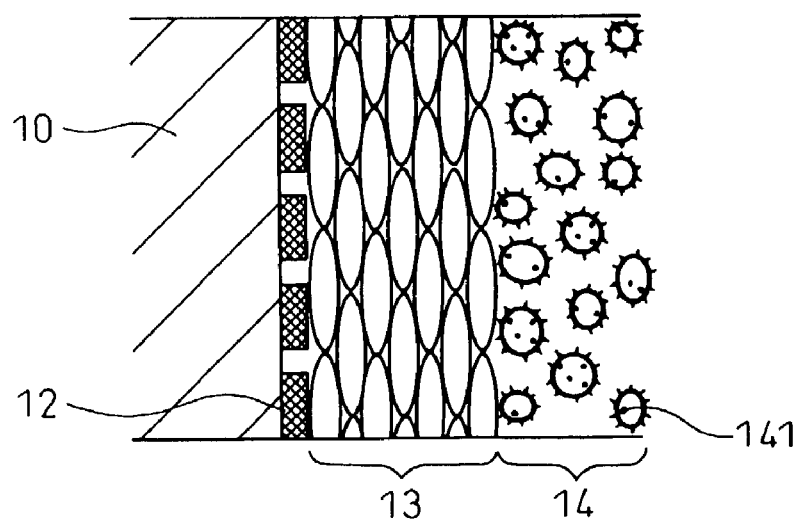
FIG. 2 is an explanatory drawing of the essential portion of the gas sensor element in Embodiment 1.

As shown in FIG. 1, gas sensor element 1 of the present embodiment is composed of a solid electrolyte 10, a measured gas side electrode 12 that contacts a measured gas provided on said solid electrolyte 10, and a reference gas side electrode 11 that contacts a reference gas, the above measured gas side electrode 12 is covered with a porous protective layer 14 composed of a heat-resistant metal oxide containing a getter 141 as shown in FIG. 2, and a porous protective layer 13 is provided between measured gas side electrode 12 and porous protective layer 14.

The following provides a detailed explanation.

Figure 3:
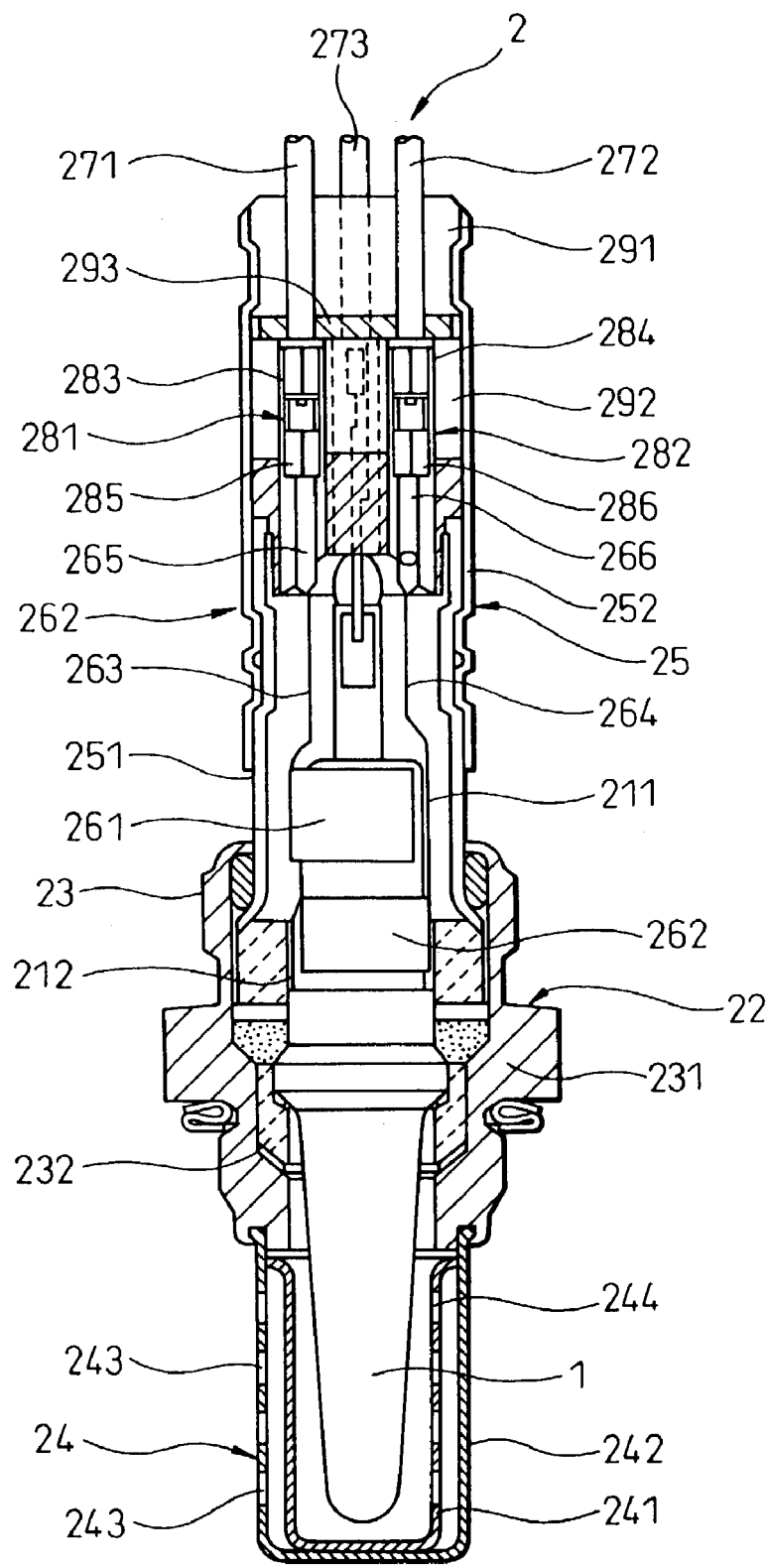
FIG. 3 is an explanatory drawing of a gas sensor containing the gas sensor element in Embodiment 1.

As shown in FIG. 2, gas sensor element 1 of the present embodiment is a cup-shaped oxygen variable concentration electromotive element having a bottomed, cylindrical shape. As shown in FIG. 3, it is contained within an oxygen sensor.

This oxygen sensor is installed in the exhaust pipe of an automobile engine, and detects the air-fuel ratio from the oxygen concentration in exhaust gas which is in an intimate relationship with the air-fuel ratio of the air-fuel mixture supplied for combustion.

As shown in FIGS. 1 and 2, gas sensor element 1 is composed of solid electrolyte and a pair of measured gas side electrode 12 and reference gas side electrode 11 provided on said solid electrolyte 10, and an electrochemical cell is composed by them. The oxygen concentration in exhaust gas is measured by this cell.

Gas sensor element 1 has porous protective layer 13, which protects the above measured gas side electrode 12 while also controlling the diffusion of measured gas, and porous protective layer 14 that covers said porous protective layer 13. In addition, the above porous protective layers are porous layers formed by flame coating of MgO. $Al_2O_3$ spinel.

As shown in FIG. 2, the above porous protective layer 14 is a porous body formed from a substrate composed of a large number of thermally stable, heat-resistant metal oxide particles in the form of alumina particles. These alumina particles form porous protective layer 14 by being continuously coupled.

The thickness of the above porous protective layer 14 is 100 μm.

In addition, the above porous protective layer 14 is composed of a mixture of coarse particles and fine particles so as to prevent the formation of cracks. The average particle diameter of the coarse particles is 15 μm, their material is $\alpha$-$Al_2O_3$, and their specific surface area is 2 m2/g, while the average particle size of the fine granules is 0.2 μm, their material is $\gamma$-$Al_2O_3$, and their specific surface area is 100 m2/g. The content of fine particles relative to the total weight of the substrate is 30 wt %.

As a result, fine particles are effectively filled into the gaps between the coarse particles, and the contact surface area with gaseous phase poisons can be increased, thereby allowing the getter contained in the porous protective layer 14 to contact the poisons.

In addition, $Li_4SiO_4$ of getter 141 is contained in porous protective layer 14 of the present embodiment, and the content of getter 141 relative to porous protective layer 14 is 20 wt %.

FIG. 3 shows an oxygen sensor 2 that contains gas sensor 1 of the present embodiment.

Oxygen sensor 2 has gas sensor element 1 that forms an electrochemical cell, and housing 22 that houses the gas sensor element 1.

The above housing 22 has body 23 provided with flange 231 approximately in its center, exhaust cover 24 below the above body 23 that is inserted into the exhaust pipe of an automobile engine, and atmospheric cover 25 above the above body 23 that contacts the atmosphere. The above exhaust cover 24 has a stainless steel inner cover 241 and an external cover 242, and has exhaust gas inlets 243 and 244 in the above inner cover 241 and outer cover 242.

On the other hand, the above atmospheric cover 25 is provided with main cover 251 attached to the above body 23, and sub cover 252 that covers the rear end of the main cover 251, and atmospheric intake ports not shown in the drawing are provided in the above main cover 251 and the above sub cover 252.

The above gas sensor element 1 is clamped inside housing 22 of the above oxygen sensor 2 interposed with insulating member 232.

In addition, metal plate terminals 261 and 262 that are clamped so as to surround a terminal portion extending from the reference gas side electrode of the above gas sensor element 1 and a terminal portion extending from the measured gas side electrode (neither are shown in the drawing) are provided on the terminals.

The above plate terminals 261 and 262 are connected to output lead wires 271 and 272.

Namely, in the above plate terminals 261 and 262, band-shaped terminal pieces 263 and 264 are provided protruding from contact pieces 265 and 266. The above terminal pieces 263 and 264 are connected to ends 285 and 286 of connectors 281 and 282 of which the other ends 283 and 284 are connected to the above lead wires 271 and 272.

With respect to the above plate terminals 261 and 262, an inverted T-shaped metal plates is deformed into the shape of a cylinder, and clamps the above terminal portion extending from the measured gas side electrode and the above terminal portion extending from the above reference gas side electrode.

A suitable contact pressure is imparted between the above plate terminals 261 and 262 and the above reference gas side electrode and the above measured gas side electrode due to the spring resiliency of the metal plate.

On the other hand, since tensile force acts on the above lead wires 271 and 272 towards the axial direction of the above oxygen sensor 2, the above plate terminals 261 and 262 may be pulled through the above connectors 281 and 282, and slide in the axial direction.

In order to prevent this, a stopper 293 interposed between rubber bushings 291 and 292 is provided in the end of the above oxygen sensor 2. Stopper 293 suppresses movement of the above connectors 281 and 282, and is formed from a resin material in order to maintain insulation between the above lead wires 271 and 272.

Furthermore, reference numeral 273 indicates a conducting wire for a heater that heats the above gas sensor element 1.

The above oxygen sensor 2 is then inserted into the exhaust pipe of an automobile engine, and is fixed in the exhaust pipe of an automobile engine by the above flange 231.

As shown in FIG. 1, the above oxygen sensor 2 having a constitution as described above contains an internal gas sensor element 1, which composes an electrochemical cell by providing a reference gas side electrode 11 and measured gas side electrode 12 on both sides of a solid electrolyte 10 serving as an oxygen ion conductor, and detects air-fuel ratio from a potential difference between the electrodes that is generated as a result of measured gas side electrode being exposed to exhaust gas, reference gas side electrode 11 being exposed to the atmosphere, and the difference in oxygen concentration of the atmosphere to which both are exposed.

The following provides an explanation of a production method of the gas sensor element 1 of the present embodiment.

To begin with, a solid electrolyte 10 of a prescribed shape is prepared, and platinum is adhered to the inner and outer surfaces by electroless plating followed by heat treatment to obtain reference gas side electrode 11 and measured gas side electrode 12.

Next, porous protective layer 13 that does not contain getter and composed of $Al_2O_3$ MgO spinel is formed by plasma coating so as to cover the surface of the above measured gas side electrode 12 and so forth. Next, porous protective layer 14 containing getter and which covers porous protective layer 13 is formed according to the procedure described below.

Water is added to $Li_4SiO_4$ serving as the raw material component of the above getter 141, and prescribed amounts of coarse particles and fine particles of the material for porous protective layer 14 are added a little at a time. Subsequently, a slurry is prepared by adding inorganic binder and dispersant at about 3–10 wt % of the total weight of the particles.

This slurry is then adhered by dipping or spraying so as to cover porous protective layer 13 formed on measured gas side electrode 12 on solid electrolyte 10, and after drying, is baked at 500–900° in a non-oxidizing atmosphere.

As a result, as shown in FIG. 2, porous protective layer 14 is obtained in which getter 141 is contained in alumina particles.

The above process is used to obtain gas sensor element 1 as claimed in the present embodiment.

According to gas sensor element 1 of the present embodiment, getter 141 composed of $Li_4SiO_4$ is contained in porous protective layer 14.

Due to its strong alkalinity, $Li_4SiO_4$ reacts with $SiO_2$ even at comparatively low temperatures, and forms stable alkaline silicate crystals having a high Si content.

At high temperatures, the alkaline silicate crystals act as crystal nuclei, and amorphous $SiO_2$ formed due to excess Si components is stably adsorbed onto the surfaces of the crystal nuclei, causing the amorphous $SiO_2$ to be crystallized and trapped.

Consequently, poisons can be trapped efficiently, and endurance is superior since clogging of porous protective layer 14 and so forth due to trapping does not occur.

As has been described above, according to the present embodiment, a gas sensor element and its production method can be provided in which poisons are trapped in a porous protective layer and prevented from reaching a measured gas side electrode, thereby making it possible to maintain stable sensor output over a long period of time.

Embodiment 2

Next, as shown in Embodiment 1, the performance of the gas sensor element as claimed in the present invention is evaluated with the following tests.

Namely, gas sensor elements having a porous protective layer that contains various getters were fabricated according to the production method indicated in Embodiment 1 while changing various parameters including the getter content, thickness of the porous protective layer and so forth. In addition, particles having a mean particle diameter of 0.1–1μm were used for the particles that compose the getter.

The endurance of each gas sensor element with respect to Si and other poisons was measured.

A list of samples used in the tests and test results are described in Table 1.

As can be determined from this table, samples 1–22 were prepared in which the content of getter relative to the porous protective layer was changed from 0–70 wt %, and the thickness of the porous protective layer was changed within the range of 20–200 μm.

In addition, Si endurance was measured according to the following procedure.

A 2000 cc, straight 4 cylinder gasoline engine equipped with a fuel injector was operated continuously at 3000 rpm. In addition, in this test, the temperature of the gas sensor elements was maintained at 600° C. by powering a heater to generate heat.

The fuel supplied to the engine consisted of gasoline containing 0.5 cc of Si oil (methyl disiloxane) per liter of gasoline.

The following provides an explanation of control λ.

Figure 4:
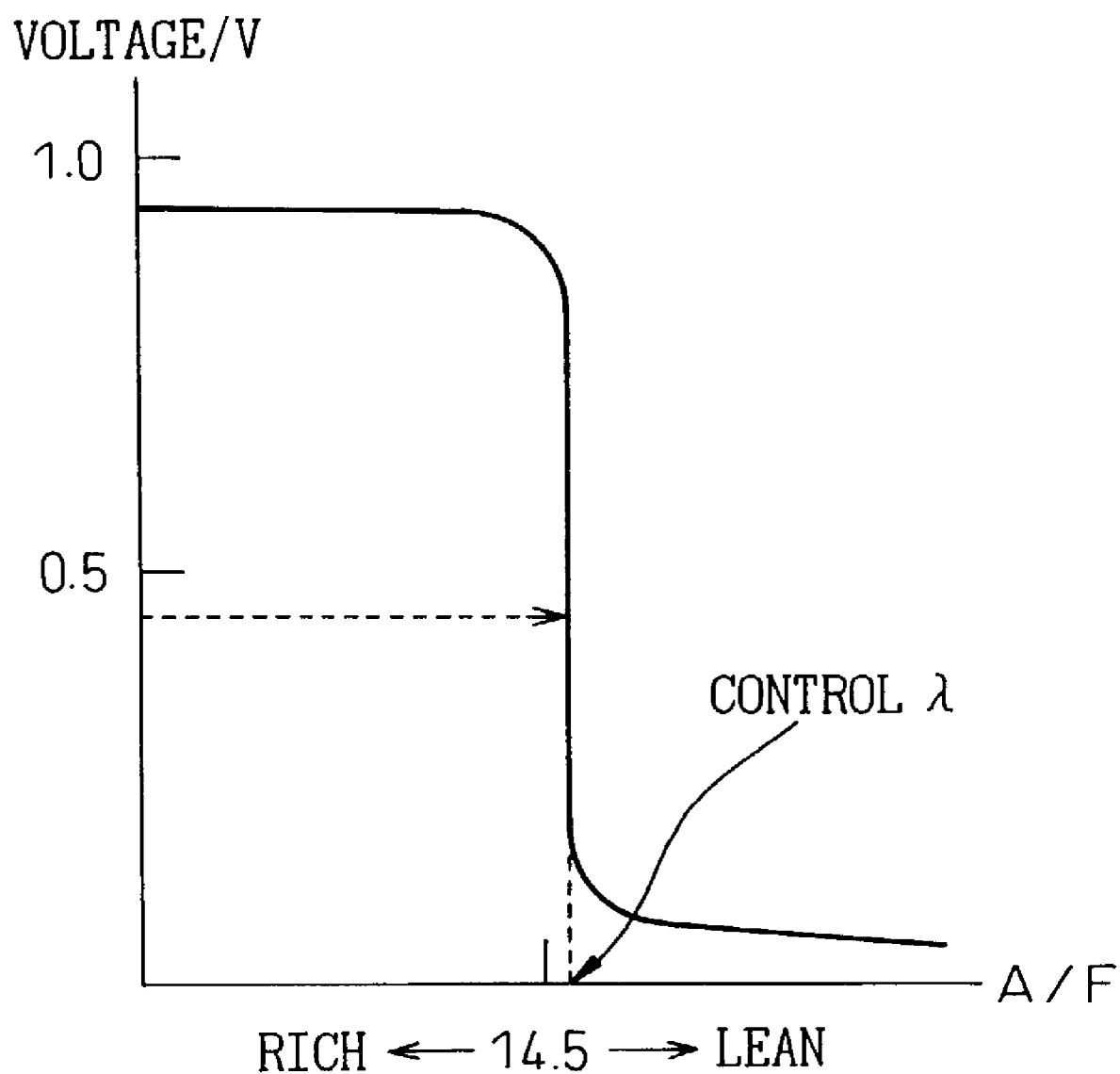
FIG. 4 is a graph showing control λ in Embodiment 2.

Although control using an oxygen sensor consists of feedback control by judging whether or the air-fuel mixture is rich or lean with respect to a reference voltage, in order to carry out said feedback control precisely, stabilization of the previously mentioned point at which λ changes suddenly (to be referred to as "control λ") is extremely important. In other words, it is important that control k always be at a specific location on the graph shown in FIG. 4 regardless of fluctuations in the external atmosphere. Furthermore, the voltage of the vertical axis of this graph is the output voltage of the gas sensor element, while A/F of the horizontal axis is the air-fuel ratio within the above engine.

In the tests of this embodiment, the gas sensor element of each sample was attached to the exhaust pipe of the above gasoline engine having a displacement of 2000 cc, the gas sensor element was heated to a temperature of 700° C. by a heater when the exhaust gas temperature was 600° C., followed by carrying out self-feedback control. Simultaneous to this, air-fuel ratio was accurately measured with a different A/F sensor attached to the exhaust pipe, and the value at that time was evaluated as the control λ point.

After measuring this control λ point for each of the new samples, each sample gas sensor element was poisoned with Si for 200 consecutive hours. Subsequently, control λ was measured according to the previously mentioned evaluation method to obtain the rate of change of control k before and after Si poisoning.

The rate of change of control λ was assessed as ⓒ for a rate of change of less than 0.1%, ○ for a rate of change of 0.1% to less than 0.3%, Δ for a rate of change of 0.3% to less than 0.4%, and X for a rate of change of 0.4% or more, and those assessments are described in Table 1.

As shown in Table 1, although clear from a comparison between sample 14 and the other samples, endurance to Si poisoning improved as a result of containing the getter of the present invention, namely alkaline silicate (samples 1–3, samples 6–13, sample 15 and sample 19), crystalline silica (samples 20–22) or compound oxide (samples 4, 5 and 16–18) in the porous protective layer.

Sample 14 that did not contain a getter exhibited poor endurance to Si poisoning, and control λ fluctuated considerably before and after endurance testing.

In addition, in a comparison of samples 1, 6 and 9, better Si poisoning endurance was determined to be able to be obtained by further increasing the getter content if the thickness of the porous protective layer is equal.

In addition, by comparing samples 1–5, it was determined that a porous protective layer having superior Si poisoning endurance can be obtained by containing a suitable amount of any of the types of getters even though there are differences among those types.

In addition, sample 13 exhibited weaker effects with respect to endurance to Si poisoning since the getter content was low at 0.2 wt %. Similarly, sample 12 exhibited similar weaker effects with respect to endurance to Si poisoning due to the reduced thickness of the porous protective layer.

Consequently, it was determined that the porous protective layer of the present embodiment preferably contains at least 0.3 wt % of getter, and that the thickness of the porous protective layer is preferably at least 20 μm.

TABLE 1

| Sample No. | Getter | Content (wt %) | Thickness of porous protective layer (μm) | Rate of change of control λ (%) | Si poisoning endurance |
|---|---|---|---|---|---|
| 1 | $Li_4SiO_4$ | 10 | 100 | 0.14 | ○ |
| 2 | $Li_2SiO_3$ | 10 | 100 | 0.14 | ○ |
| 3 | $Li_2Si_2O_5$ | 10 | 100 | 0.21 | ○ |
| 4 | $Li_2WO_4$ | 10 | 100 | 0.21 | ○ |
| 5 | $Li_2MoO_4$ | 10 | 100 | 0.21 | ○ |
| 6 | $Li_4SiO_4$ | 1 | 100 | 0.27 | ○ |
| 7 | $Li_4SiO_4$ | 0.5 | 200 | 0.27 | ○ |
| 8 | $Li_2SiO_3$ | 5 | 200 | 0.07 | ◎ |
| 9 | $Li_4SiO_4$ | 20 | 100 | 0.07 | ◎ |
| 10 | $Li_2SiO_3$ | 10 | 200 | 0.07 | ◎ |
| 11 | $Li_2SiO_3$ | 30 | 50 | 0.27 | ○ |
| 12 | $Li_4SiO_4$ | 50 | 10 | 0.34 | Δ |
| 13 | $Li_2SiO_3$ | 0.2 | 200 | 0.34 | Δ |
| 14 | — | 0 | 200 | 0.48 | X |
| 15 | $Li_2SiO_3$ | 5 | 100 | 0.21 | ○ |
| 16 | $Li_2WO_4$ | 20 | 100 | 0.14 | ○ |
| 17 | $Li_2WO_4$ | 10 | 200 | 0.07 | ◎ |
| 18 | $Li_2MoO_4$ | 50 | 100 | 0.07 | ◎ |
| 19 | $Li_2SiO_3$ | 70 | 50 | 0.07 | ◎ |
| 20 | $SiO_2$ (cristobalite) | 20 | 200 | 0.14 | ○ |
| 21 | $SiO_2$ (cristobalite) | 60 | 20 | 0.27 | ○ |
| 22 | $SiO_2$ (cristobalite) | 0.3 | 200 | 0.28 | ○ |

Embodiment 3

Figure 5:
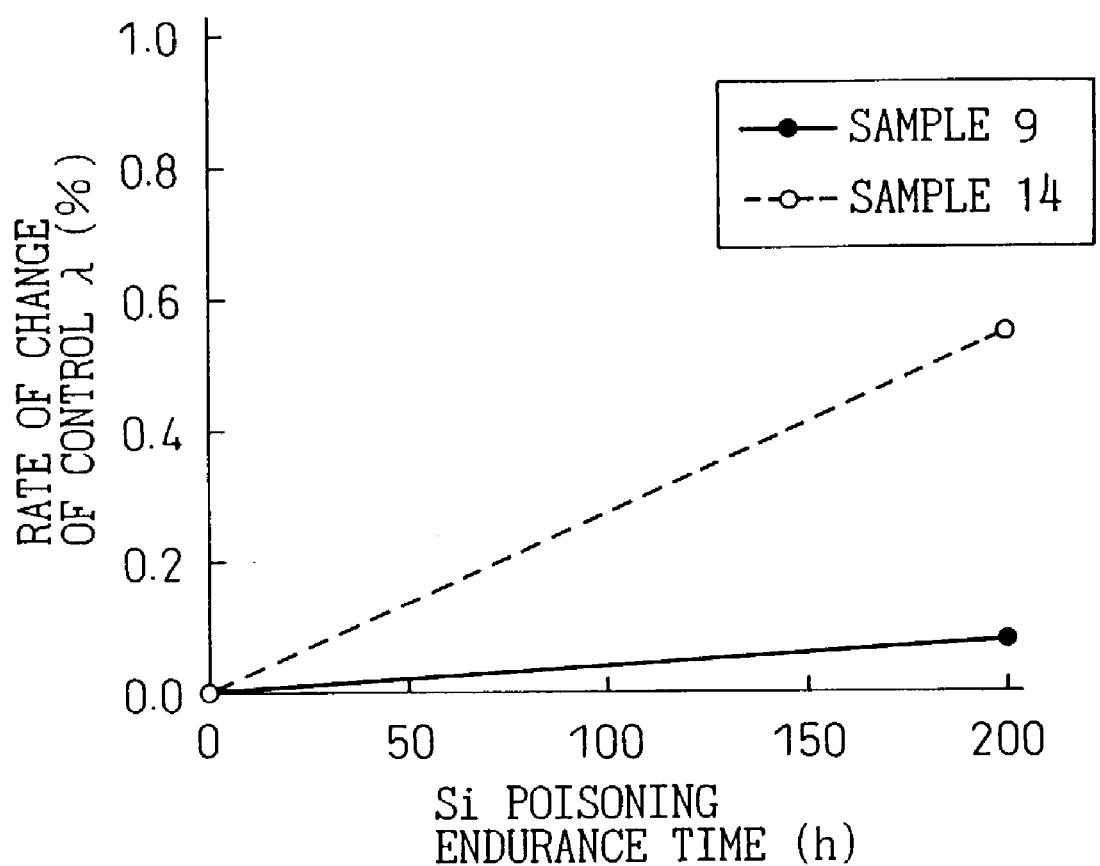
FIG. 5 is a graph showing the relationship between the rate of change of control λ and the Si poisoning endurance time in Embodiment 3.

FIG. 5 describes the relationship between control k and Si poisoning time for samples 9 and 14 described in Embodiment 2.

As is known from the FIG. 5, there was hardly any change in control λ despite increased Si poisoning time for sample 9 provided with a porous protective layer containing a getter a claimed in the present invention. However, in sample 14 that is not provided with a getter, control λ was found to change considerably together with increased Si poisoning time.

In this manner, it was determined that a gas sensor element can be composed to have superior endurance without hardly any changes in gas sensor element characteristics before and after poisoning endurance by containing a getter a claimed in the present invention in a porous protective layer.

Embodiment 4

The gas sensor element as claimed in the present embodiment is a sensor provided with a protective porous layer so as to cover a measured gas side electrode.

Figure 6:
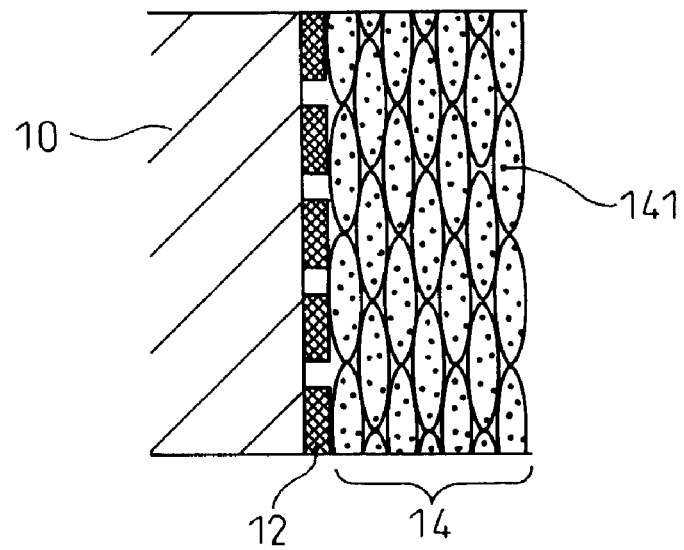
FIG. 6 is an explanatory drawing of the essential portion of a gas sensor element provided with a porous protective layer directly on the surface of a measured gas side electrode in Embodiment 4.

As shown in FIG. 6, a flame coated layer was provided on the surface of a measured gas side electrode 12 by flame coating of heat-resistant metal oxide. A porous protective layer 14 was then formed by subsequently retaining getter 141.

The performance of a gas sensor element fabricated in this manner was tested using the same method as Embodiment 2.

A list of the samples used in this test along with the test results are described in Table 2.

As can be determined from Table 2, samples L1–L14 were prepared in which the getter content relative to the porous protective layer was changed from 0–20 wt %, and the thickness of the porous protective layer was changed within the range of 30–300 μm.

The Si poisoning endurance of these samples was judged in the same manner as Embodiment 2 by assessing the rate of change of control λ was assessed as ⊚ for a rate of change of less than 0.1%, ○ for a rate of change of 0.1% to less than 0.3%, Δ for a rate of change of 0.3% to less than 0.4%, and X for a rate of change of 0.4% or more.

As can be determined from this table, Si poisoning endurance improved as a result of containing a getter in the porous protective layer. Sample L14, which did not contain a getter, exhibited poor Si poisoning endurance, and control λ fluctuated considerably before and after endurance testing.

In addition, sample 13 exhibited weaker effects with respect to endurance to Si poisoning since the getter content was low at 0.2 wt %. Similarly, sample 12 exhibited similar weaker effects with respect to endurance to Si poisoning due to the reduced thickness of the porous protective layer.

Consequently, it was determined that the porous protective layer of the present embodiment preferably contains at least 0.3 wt % of getter, and that the thickness of the porous protective layer is preferably at least 50 μm.

TABLE 2

| Sample No. | Getter | Content (wt %) | Thickness of porous protective layer (μm) | Rate of change of control λ (%) | Si poisoning endurance |
|---|---|---|---|---|---|
| L1 | $Li_4SiO_4$ | 5 | 200 | 0.14 | ○ |
| L2 | $Li_2SiO_3$ | 5 | 200 | 0.14 | ○ |
| L3 | $SiO_2$ (cristobalite) | 5 | 200 | 0.21 | ○ |
| L4 | $Li_2WO_4$ | 5 | 200 | 0.21 | ○ |
| L5 | $Li_2MoO_4$ | 5 | 200 | 0.21 | ○ |
| L6 | $Li_2SiO_3$ | 1 | 200 | 0.27 | ○ |
| L7 | $Li_2SiO_3$ | 0.3 | 200 | 0.27 | ○ |
| L8 | $Li_2SiO_3$ | 10 | 300 | 0.07 | ⊚ |
| L9 | $Li_4SiO_4$ | 15 | 200 | 0.07 | ⊚ |
| L10 | $SiO_2$ (cristobalite) | 20 | 100 | 0.14 | ○ |
| L11 | $SiO_2$ (cristobalite) | 20 | 50 | 0.27 | ○ |
| L12 | $SiO_2$ (cristobalite) | 20 | 10 | 0.34 | Δ |
| L13 | $Li_2SiO_3$ | 0.2 | 200 | 0.34 | Δ |
| L14 | — | 0 | 300 | 0.48 | X |

Embodiment 5

The present embodiment provides an explanation of a production method of a gas sensor element in which a porous protective layer containing a getter directly covers the surface of a measured gas side electrode.

A solid electrolyte having a prescribed shape was prepared, platinum was adhered to the inner and outer surfaces by electroless plating followed by heat treatment to obtain a reference gas side electrode and a measured gas side electrode.

Next, a porous protective layer that does not contain getter and composed of $Al_2O_3 \cdot MgO$ spinel was formed by plasma coating so as to cover the surface of the above measured gas side electrode and so forth.

Subsequently, a solution containing a getter raw material component to serve as the getter was impregnated into the porous protective layer. $Li_4SiO_4$ was used for the getter raw material component, and water was used for the solvent. In addition, impregnation was realized by dipping into the above solution.

This was followed by drying and heat treatment to obtain a porous protective layer composed of a heat-resistant metal oxide containing a getter.

When the performance of the gas sensor element fabricated in this manner was evaluated according to the method indicated in Embodiment 2, results similar to those of sample 1 were obtained in which a gas sensor element containing 10 wt % of $Li_4SiO_4$ and having a protective layer thickness of 100 μm exhibited a rate of change of control λ of 14% and an assessment of Si poisoning endurance of ⊚.

In this manner, a gas sensor element having superior responsiveness was determined to be obtained from the production method as claimed in the present embodiment.

Embodiment 6

Similar to Embodiment 5, the present embodiment also provides an explanation of a production method of a gas sensor element in which a porous protective layer containing a getter directly covers a measured gas side electrode.

A solid electrolyte having a prescribed shape was prepared, platinum was adhered to the inner and outer surfaces by electroless plating followed by heat treatment to obtain a reference gas side electrode and a measured gas side electrode.

Next, a material for a porous protective layer composed of a heat-resistant metal oxide containing a getter raw material component was loaded into a plasma jet and melted followed by spraying onto the above measured gas side electrode (this is plasma coating) to obtain a porous protective layer. In addition, $Li_4SiO_4$ was used for the getter raw material component, and $MgAl_2O_4$ was used for the material for the porous protective layer.

When the performance of the gas sensor element fabricated in this manner was evaluated according to the method indicated in Embodiment 2, results similar to those of sample 1 were obtained in which a gas sensor element containing 10 wt % of $Li_4SiO_4$ and having a protective layer thickness of 100 μm exhibited a rate of change of control k of 14% and an assessment of Si poisoning endurance of ◯.

In this manner, a gas sensor element having superior responsiveness was determined to be obtained from the production method as claimed in the present embodiment.

What is claimed is:

1. A gas sensor element comprising: a solid electrolyte, and a measured gas side electrode that contacts a measured gas and a reference gas side electrode that contacts a reference gas provided on said solid electrolyte; wherein, the above measured gas side electrode is covered with a porous protective layer composed of a heat-resistant metal oxide containing a getter, and the above getter is an alkaline silicate.

2. The gas sensor element according to claim 1 wherein, the above alkaline silicate is one or more types selected from lithium orthosilicate ($Li_4SiO_4$), lithium metasilicate ($Li_2SiO_3$), lithium disilicate ($Li_2Si_2O_3$), hexalithium disilicate ($Li_6Si_2O_7$), $Li_2Si_3O_7$ and $Li_8SiO_6$.

3. The sensor element according to claim 1 wherein, the content of the above getter with respect to the above porous protective layer composed of a heat-resistant metal oxide is 0.3–70 wt %.

4. The gas sensor element according to claim 1 wherein, the thickness of the above porous protective layer composed of a heat-resistant metal oxide is 20–300 μm.

5. The gas sensor according to claim 1 wherein, the average particle diameter of the above getter is 0.1–1 μm.

6. The gas sensor element according to claim 1 wherein, the above porous protective layer composed of a heat-resistant metal oxide contains a matrix composed of one or more types of particulate material selected from γ-$Al_2O_3$, θ-$Al_2O_3$ and δ-$Al_2O_3$.

7. The gas sensor element according to claim 1 wherein, said gas sensor element has at least one porous protective layer composed of a heat-resistant metal oxide that contains a getter in direct contact with the above measured gas side electrode.

8. The gas sensor element according to claim 1 wherein, said gas sensor element has another porous protective layer composed of a heat-resistant metal oxide that does not contain a getter between the above measured gas side electrode and the above porous protective layer composed of a heat-resistant metal oxide.

9. A gas sensor element comprising: a solid electrolyte, and a measured gas side electrode that contacts a measured gas and a reference gas side electrode that contacts a reference gas provided on said solid electrolyte; wherein, the above measured gas side electrode is covered with a porous protective layer composed of a heat-resistant metal oxide containing a getter, and the above getter is composed of both alkaline silicate and crystalline silica.

10. A gas sensor element comprising: a solid electrolyte, and a measured gas side electrode that contacts a measured gas and a reference gas side electrode that contacts a reference gas provided on said solid electrolyte; wherein, the above measured gas side electrode is covered with a porous protective layer composed of a heat-resistant metal oxide containing a getter, the above getter is a compound oxide, and, said compound oxide is composed of an alkaline metal oxide and a pentavalent or hexavalent transition metal oxide.

11. The gas sensor element according to claim 10 wherein, the above compound oxide is a tungstenate salt of an alkaline metal or a molybdenate compound of an alkaline metal.

12. The gas sensor element according to claim 11 wherein, the above compound oxide is one or more types selected from $Li_2W_4O_{13}$, $Li_2W_2O_7$, $Li_2WO_4$, $Li_4WO_5$, $Li_6W_2O_9$, $Li_2WO_6$, $Li_6WO_6$, $Li_2MoO_4$, $Li_2MO_4O_{13}$, $Li_4MoO_5$ and $Li_2Mo_2O_7$.

* * * * *